US010349847B2

United States Patent
Kwon et al.

(10) Patent No.: US 10,349,847 B2
(45) Date of Patent: Jul. 16, 2019

(54) APPARATUS FOR DETECTING BIO-INFORMATION

(71) Applicant: SAMSUNG ELECTRONICS CO., LTD., Suwon-si (KR)

(72) Inventors: Yongjoo Kwon, Yongin-si (KR); Youngzoon Yoon, Hwaseong-si (KR); Seongho Cho, Gwacheon-si (KR); Jaemin Kang, Seoul (KR); Sunkwon Kim, Suwon-si (KR); Younho Kim, Hwaseong-si (KR); Sangyun Park, Hwaseong-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 350 days.

(21) Appl. No.: 14/818,420

(22) Filed: Aug. 5, 2015

(65) Prior Publication Data

US 2016/0206251 A1 Jul. 21, 2016

(30) Foreign Application Priority Data

Jan. 15, 2015 (KR) .......................... 10-2015-0007445

(51) Int. Cl.
*A61B 5/02* (2006.01)
*A61B 5/024* (2006.01)
(Continued)

(52) U.S. Cl.
CPC ...... *A61B 5/02427* (2013.01); *A61B 5/14552* (2013.01); *A61B 5/02007* (2013.01);
(Continued)

(58) Field of Classification Search
CPC ............ A61B 2562/04; A61B 5/02007; A61B 5/02108; A61B 5/02427; A61B 5/0261; A61B 5/14552; A61B 5/6824
See application file for complete search history.

(56) References Cited

U.S. PATENT DOCUMENTS

| | | | |
|---|---|---|---|
| 4,987,900 A | 1/1991 | Eckerle et al. | |
| 5,065,765 A | 11/1991 | Eckerle et al. | |

(Continued)

FOREIGN PATENT DOCUMENTS

| | | |
|---|---|---|
| CN | 104257371 A | 1/2015 |
| CN | 10-4970781 A | 10/2015 |

(Continued)

OTHER PUBLICATIONS

Communication dated Dec. 14, 2017 issued by the European Patent Office in counterpart Application No. 17172684.7.

(Continued)

*Primary Examiner* — Amanda K Hulbert
(74) *Attorney, Agent, or Firm* — Sughrue Mion, PLLC

(57) ABSTRACT

An apparatus and a method for detecting bio-information are provided. The apparatus includes a bio-signal detector including a light emitter including a light-emitting diode (LED) and a laser diode (LD), the LED and the LD being configured to emit optical signals on an object. The bio-signal detector further includes an optical detector including a light-receiver configured to detect optical signals modulated by the object. The apparatus further includes a processor configured to process the optical signals to detect the bio-information of the object.

16 Claims, 9 Drawing Sheets

(51) Int. Cl.
  *A61B 5/1455* (2006.01)
  *A61B 5/026* (2006.01)
  *A61B 5/021* (2006.01)
  *A61B 5/00* (2006.01)

(52) U.S. Cl.
  CPC ......... *A61B 5/0261* (2013.01); *A61B 5/02108* (2013.01); *A61B 5/6824* (2013.01); *A61B 2562/04* (2013.01)

(56) References Cited

U.S. PATENT DOCUMENTS

| | | | |
|---|---|---|---|
| 5,265,011 A | 11/1993 | O'Rourke | |
| 5,891,022 A | 4/1999 | Pologe | |
| 6,161,038 A | 12/2000 | Schookin et al. | |
| 6,475,153 B1 | 11/2002 | Khair et al. | |
| 6,571,193 B1 | 5/2003 | Unuma et al. | |
| 7,123,363 B2 | 10/2006 | Puttappa et al. | |
| 7,231,243 B2 | 6/2007 | Tearney et al. | |
| 7,463,796 B2 | 12/2008 | Borgos et al. | |
| 7,641,614 B2 | 1/2010 | Asada et al. | |
| 7,657,135 B2 | 2/2010 | Borgos et al. | |
| 7,737,947 B2 | 6/2010 | Schroeder et al. | |
| 7,822,299 B2 | 10/2010 | Borgos et al. | |
| 7,925,056 B2 | 4/2011 | Presura et al. | |
| 8,032,200 B2 | 10/2011 | Tearney et al. | |
| 8,089,465 B2 | 1/2012 | Lutian | |
| 8,111,953 B2 | 2/2012 | Borgos et al. | |
| 8,217,897 B2 | 7/2012 | Lutian | |
| 8,277,384 B2 | 10/2012 | Fine | |
| 8,313,439 B2 | 11/2012 | McCombie et al. | |
| 8,343,062 B2 | 1/2013 | Fortin et al. | |
| 8,343,063 B2 | 1/2013 | Borgos | |
| 8,360,985 B2 | 1/2013 | Borgos | |
| 8,467,636 B2 | 6/2013 | Borgos et al. | |
| 8,496,595 B2 | 7/2013 | Jornod | |
| 8,808,188 B2 | 8/2014 | Banet et al. | |
| 8,868,149 B2 | 10/2014 | Eisen et al. | |
| 8,954,135 B2 | 2/2015 | Yuen et al. | |
| 9,097,516 B2 | 8/2015 | Hotta et al. | |
| 9,149,216 B2 | 10/2015 | Eisen et al. | |
| 9,277,868 B2 | 3/2016 | Borgos et al. | |
| 9,282,931 B2 | 3/2016 | Tearney et al. | |
| 9,326,711 B2* | 5/2016 | Kracker | A61B 5/14542 |
| 9,510,758 B2 | 12/2016 | Warger, II et al. | |
| 9,596,990 B2 | 3/2017 | Park et al. | |
| 9,603,524 B2 | 3/2017 | Park et al. | |
| 9,636,041 B2 | 5/2017 | Zalevsky et al. | |
| 9,668,672 B2 | 6/2017 | Zalevsky et al. | |
| 9,704,050 B2 | 7/2017 | Lee et al. | |
| 2002/0007125 A1 | 1/2002 | Hickey | |
| 2002/0095092 A1* | 7/2002 | Kondo | A61B 5/02116 600/503 |
| 2003/0013976 A1 | 1/2003 | Freund et al. | |
| 2004/0186387 A1 | 9/2004 | Kosuda et al. | |
| 2005/0228297 A1 | 10/2005 | Banet et al. | |
| 2007/0078308 A1 | 4/2007 | Daly | |
| 2007/0163353 A1 | 7/2007 | Lec et al. | |
| 2007/0265533 A1 | 11/2007 | Tran | |
| 2007/0276262 A1 | 11/2007 | Banet et al. | |
| 2007/0276632 A1 | 11/2007 | Banet et al. | |
| 2008/0071180 A1 | 3/2008 | Borgos | |
| 2008/0146952 A1 | 6/2008 | Presura et al. | |
| 2008/0181556 A1 | 7/2008 | Borgos et al. | |
| 2008/0183053 A1 | 7/2008 | Borgos et al. | |
| 2008/0228089 A1 | 9/2008 | Cho et al. | |
| 2009/0069698 A1 | 3/2009 | Bae et al. | |
| 2009/0073461 A1 | 3/2009 | Borgos et al. | |
| 2009/0209834 A1 | 8/2009 | Fine | |
| 2009/0209871 A1 | 8/2009 | Ueki et al. | |
| 2009/0326393 A1 | 12/2009 | Sethi et al. | |
| 2010/0022861 A1* | 1/2010 | Cinbis | A61B 5/0084 600/325 |
| 2010/0049059 A1 | 2/2010 | Ha et al. | |
| 2010/0145171 A1 | 6/2010 | Park et al. | |
| 2010/0160798 A1 | 6/2010 | Banet et al. | |
| 2010/0168589 A1 | 7/2010 | Banet et al. | |
| 2010/0210930 A1 | 8/2010 | Saylor | |
| 2010/0210956 A1 | 8/2010 | Im | |
| 2010/0324384 A1 | 12/2010 | Moon et al. | |
| 2011/0021931 A1 | 1/2011 | Borgos et al. | |
| 2011/0172505 A1 | 7/2011 | Kim et al. | |
| 2011/0208066 A1 | 8/2011 | Gnadinger | |
| 2012/0025185 A1 | 2/2012 | Kasamatsu | |
| 2012/0108956 A1 | 5/2012 | Warger, II et al. | |
| 2012/0130215 A1 | 5/2012 | Fine et al. | |
| 2012/0130253 A1 | 5/2012 | Nadkarni et al. | |
| 2012/0130260 A1 | 5/2012 | Borgos et al. | |
| 2012/0136261 A1 | 5/2012 | Sethi et al. | |
| 2012/0143066 A1 | 6/2012 | Antonelli et al. | |
| 2012/0191001 A1 | 7/2012 | Segman | |
| 2013/0046192 A1* | 2/2013 | Lin | A61B 5/02007 600/500 |
| 2013/0131475 A1 | 5/2013 | Eisen et al. | |
| 2013/0144137 A1 | 6/2013 | Zalevsky et al. | |
| 2013/0190630 A1 | 7/2013 | Borgos | |
| 2013/0218025 A1 | 8/2013 | Tverskoy | |
| 2013/0245456 A1 | 9/2013 | Ferguson, Jr. et al. | |
| 2014/0012146 A1 | 1/2014 | Fukuda | |
| 2014/0066788 A1 | 3/2014 | Mukkamala et al. | |
| 2014/0066793 A1 | 3/2014 | Mukkamala et al. | |
| 2014/0081153 A1* | 3/2014 | Kuno | A61B 5/02427 600/479 |
| 2014/0107493 A1 | 4/2014 | Yuen et al. | |
| 2014/0125491 A1 | 5/2014 | Park et al. | |
| 2014/0127996 A1 | 5/2014 | Park et al. | |
| 2014/0148658 A1 | 5/2014 | Zalevsky et al. | |
| 2014/0200423 A1 | 7/2014 | Eisen et al. | |
| 2014/0288435 A1 | 9/2014 | Richards et al. | |
| 2015/0105638 A1 | 4/2015 | Eisen et al. | |
| 2015/0117015 A1 | 4/2015 | Roh et al. | |
| 2015/0119725 A1 | 4/2015 | Martin et al. | |
| 2015/0126820 A1 | 5/2015 | Muhlsteff | |
| 2015/0323311 A1 | 11/2015 | Muijs et al. | |
| 2016/0058300 A1 | 3/2016 | Yoon et al. | |
| 2016/0066790 A1 | 3/2016 | Shcherbakov et al. | |
| 2016/0103985 A1 | 4/2016 | Shim et al. | |
| 2016/0106325 A1 | 4/2016 | Kang et al. | |
| 2016/0106327 A1 | 4/2016 | Yoon et al. | |
| 2016/0106333 A1 | 4/2016 | Kang et al. | |
| 2016/0113589 A1 | 4/2016 | Yoon | |
| 2016/0157736 A1 | 6/2016 | Huang et al. | |
| 2016/0192845 A1 | 7/2016 | Warger et al. | |
| 2016/0198961 A1 | 7/2016 | Homyk et al. | |
| 2016/0206251 A1 | 7/2016 | Kwon et al. | |
| 2016/0256116 A1 | 9/2016 | Baik et al. | |
| 2016/0256117 A1 | 9/2016 | Baik et al. | |
| 2016/0278645 A1 | 9/2016 | Yoon | |
| 2016/0278718 A1 | 9/2016 | Fujii et al. | |
| 2016/0287109 A1 | 10/2016 | Shim et al. | |
| 2016/0357154 A1 | 12/2016 | Shim et al. | |
| 2017/0017858 A1 | 1/2017 | Roh et al. | |
| 2017/0049340 A1 | 2/2017 | Cho et al. | |
| 2017/0055855 A1 | 3/2017 | Yoon | |
| 2017/0065184 A1 | 3/2017 | Barak | |
| 2017/0105679 A1 | 4/2017 | Gil | |
| 2017/0112395 A1 | 4/2017 | Kim et al. | |
| 2017/0135636 A1 | 5/2017 | Park et al. | |
| 2017/0150930 A1 | 6/2017 | Shikii et al. | |
| 2017/0172510 A1 | 6/2017 | Homyk et al. | |
| 2017/0209047 A1 | 7/2017 | Zalevsky et al. | |
| 2017/0245796 A1 | 8/2017 | Zalevsky et al. | |
| 2017/0251926 A1 | 9/2017 | Yoon et al. | |
| 2017/0319146 A1 | 11/2017 | Park et al. | |

FOREIGN PATENT DOCUMENTS

| | | |
|---|---|---|
| DE | 10 2010 014 761 A1 | 10/2011 |
| EP | 0755221 B1 | 10/2001 |
| EP | 1 204 370 B1 | 4/2008 |
| EP | 3072441 A1 | 9/2016 |
| JP | 11-155826 A | 6/1999 |
| JP | 2000-166885 A | 6/2000 |
| JP | 2003-532478 A | 11/2003 |

(56) References Cited

FOREIGN PATENT DOCUMENTS

| | | |
|---|---|---|
| JP | 3769524 B2 | 4/2006 |
| JP | 2008-295576 A | 12/2008 |
| JP | 4506849 B2 | 7/2010 |
| JP | 4614184 B2 | 1/2011 |
| JP | 4645259 B2 | 3/2011 |
| JP | 4848732 B2 | 12/2011 |
| JP | 2012-57962 A | 3/2012 |
| JP | 2012-161507 A | 8/2012 |
| JP | 2012-187300 A | 10/2012 |
| JP | 2012-202776 A | 10/2012 |
| JP | 2013-509225 A | 3/2013 |
| JP | 2014-23031 A | 2/2014 |
| JP | 5528816 B2 | 6/2014 |
| JP | 2014240782 A | 12/2014 |
| JP | 2015-502197 A | 1/2015 |
| KR | 10-0610813 B1 | 8/2006 |
| KR | 10-0650044 B1 | 11/2006 |
| KR | 10-2008-0073988 A | 8/2008 |
| KR | 10-2009-0052442 A | 5/2009 |
| KR | 10-2010-0060141 A | 6/2010 |
| KR | 10-2010-0065084 A | 6/2010 |
| KR | 10-1007354 B1 | 1/2011 |
| KR | 1020110025100 A | 3/2011 |
| KR | 10-1040598 B1 | 6/2011 |
| KR | 10-1058152 B1 | 8/2011 |
| KR | 10-1065615 B1 | 9/2011 |
| KR | 10-2012-0057813 A | 6/2012 |
| KR | 10-1310464 B1 | 9/2013 |
| KR | 10-2014-0024845 A | 3/2014 |
| KR | 10-1503604 B1 | 3/2015 |
| KR | 10-1560287 B1 | 10/2015 |
| KR | 10-1564066 B1 | 10/2015 |
| KR | 10-2016-0041553 A | 4/2016 |
| KR | 10-2016-0088127 A | 7/2016 |
| KR | 10-2016-0107007 A | 9/2016 |
| KR | 10-2016-0108081 A | 9/2016 |
| KR | 10-2017-0104361 A | 9/2017 |
| KR | 10-2017-0124943 A | 11/2017 |
| WO | 2015/129949 A1 | 9/2015 |

OTHER PUBLICATIONS

Zhang et al., "A LabVIEW Based Measure System for Pulse Wave Transit Time"; Proceedings of the 5th International Conference on Information Technology and Application in Biomedicine, in conjunction with The 2nd International Symposium & Summer School on Biomedical and Health Engineering; May 30-31, 2008; 4 pgs. Total, pp. 477-480.
Yan et al., "Noninvasive Estimation of Blood Pressure Using Photophlethysmographic Signals in the Period Domain"; Proceedings of the 2005 IEEE Engineering in Medicine and Biology 27th Annual Conference; Sep. 1-4, 2005; pp. 3583-3584, 2 pgs. total.
Fortino et al., "PPG-based Methods for Non Invasive and Continuous Blood Pressure Measurement: an Overview and Development Issues in Body Sensor Networks"; IEEE; 2010; 4 pgs. total.
Kurylyak, et al., "A Neural Network-based Method for Continuous Blood Pressure Estimation from a PPG Signal"; Instrumentation and Measurement Technology Conference (I2MTC); May 6-9, 2013; 4pgs. Total, pp. 280-283.
Teng et al., "Continuous and Noninvasive Estimation of Arterial Blood Pressure Using a Photoplethysmographic Approach"; Proceedings of the 25th Annual International Conference of the IEEE EMBS; Sep. 17-21, 2003; 4 pgs. Total, pp. 3153-3156.
Young-Zoon Yoon.,"Study on cardiovascular system with blood pressure waveform and heart rate variability", A Dissertation Submitted to the Faculty of Seoul National University in Partial Fulfillment of the Requirements for the Degree of Doctor of Philosophy, School of Physics, Graduate School, Seoul National University, 2005, (210 Pages Total).
Chen et al., "Estimation of Central Aortic Pressure Waveform by Mathematical Transformation of Radial Tonometry Pressure; Validation of Generalized Transfer Function", 1997: 95, 1827-36, 12 pages total, American Heart Association.
O'Rourke et al., "Pulse wave analysis", Research Methods in Human Cardiovascular Pharmacology, 2001, Clinical Pharmacology, Blackwell Science Ltd Br J Clin Pharmacol: 51, pp. 507-522, 16 pages total.
Aymen A. Awad et al., "How Does the Plethysmogram Derived from the Pulse Oximeter Relate to Arterial Blood Pressure in Coronary Artery Bypass Graft Patients?"; Anesth Analg, 93; 2001; pp. 1466-1471; 6 pgs. total.
Satomi Suzuki, et al., "Cuffless and Non-invasive Systolic Blood Pressure Estimation for Aged Class by Using a Photoplethysmograph"; 30th Annual International IEEE EMBS Conference; Aug. 20-24, 2008; pp. 1327-1330; 4 pgs. total.
Arata Suzuki et al., "Feature Selection Method for Estimating Systolic Blood Pressure Using the Taguchi Method"; IEEE Transactions on Industrial Informatics; vol. 10; No. 2; May 2014; pp. 1077-1085; 9 pgs. total.
Y. Kurylyak et al., "Photoplethysmogram-based Blood Pressure Evaluation using Kalman Filtering and Neural Networks"; Medical Measurements and Applications Proceedings (MeMeA), 2013 IEEE International Symposium; May 4, 2013; 5 pgs. total.
Yevgeny Beiderman et al., "Remote estimation of blood pulse pressure via temporal tracking of reflected secondary speckles pattern"; Journal of Biomedical Optics; vol. 15; No. 6; Nov./Dec. 2010; pp. 061707-1-061707-7; 7 pgs. total.
Yu.N. Kul'Chin et al., "Correlation method for processing speckles of signals from single-fibre multimode interferometers by using charge-coupled devices"; Optical Fibres and Waveguides; Quantum Electronics; vol. 36; No. 4; 2006; pp. 339-342; 5 pgs. total.
Enric Monte-Moreno., "Non-invasive estimate of blood glucose and blood pressure from a photoplethysmograph by means of machine learning techniques", Artificial Intelligence in Medicine, vol. 53, 2011, pp. 127-138, 12 Pages total.
Communication dated Aug. 30, 2016 issued by the European Patent Office in counterpart European Patent Application No. 16158751.4.
Ramakrishna Mukkamala et al., "Towards Ubiquitous Blood Pressure Monitoring via Pulse Transit Time: Theory and Practice", IEEE Trans Biomed Eng. Aug. 2015 ; 62(8), pp. 1879-1901, 48 pages total.
Qing Liu et al., "Attenuation of Systolic Blood Pressure and Pulse Transit Time Hysteresis During Exercise and Recovery in Cardiovascular Patients", IEEE Transactions on Biomedical Engineering, vol. 61, No. 2, Feb. 2014, pp. 346-352.
R. A. Payne et al., "Pulse transit time measured from the ECG: an unreliable marker of beat-to-beat blood pressure", J Appl Physiol, the American Physiological Society 100, 2006, pp. 136-141.
Communication from United States Patent and Trademark Office issued Jun. 28, 2017, in U.S. Appl. No. 14/844,437.
Communication from United States Patent and Trademark Office issued Apr. 17, 2017, in U.S. Appl. No. 15/068,760.
Jianjun Qiu et al; "Spatiotemporal laser speckle contrast analysis for blood flow imaging with maximized speckle contrast"; Journal of Biomedical Optics; vol. 15; No. 1; Jan./Feb. 2010; pp. 016003-1-016003-5; 5pgs. total.
Dr. S. Shah et al; "Optoelectronic blood pressure estimation: A novel principle for blood pressure measurement"; Tarilian Laser Technologies; (http://www.tarilian-lasertechnologies.com/press/tlt-at-esh2012.php); 2012; 4 pgs. total.
"Tarilian Laser Technologies achieves greatest technological advance in blood pressure measurement for 130 years"; (http://www.tarilian-lasertechnologies.com/press/pr111201.php); Tarilian Laser Technologies; Dec. 7, 2011; 6 pgs. total.
Final Office Action dated Jul. 16, 2018 by the United States Patent and Trademark Office in U.S. Appl. No. 15/068,760.
Final Office Action dated May 23, 2018 by United States Patent and Trademark Office in U.S. Appl. No. 14/862,288.
Non-Final Office Action dated May 25, 2018 by United States Patent and Trademark Office in U.S. Appl. No. 14/961,145.
Notice of Allowance dated Nov. 7, 2018, issued by United States Patent and Trademark Office in U.S. Appl. No. 14/844,437.
Notice of Allowance dated Oct. 24, 2018, issued by United States Patent and Trademark Office in U.S. Appl. No. 15/068,760.

(56) References Cited

OTHER PUBLICATIONS

Restriction Requirement dated Sep. 6, 2018 issued by the United States Patent and Trademark Office in U.S. Appl. No. 14/884,019.
Advisory Action dated Aug. 2, 2018 by the United States Patent and Trademark Office in U.S. Appl. No. 14/862,288.
Non-Final Office Action dated Jul. 26, 2018 by the United States Patent and Trademark Office in U.S. Appl. No. 14/833,221.
Non-Final Office Action dated Jun. 15, 2018 by the U.S. Patent and Trademark Office in U.S. Appl. No. 14/844,437.
Final Office Action dated Feb. 28, 2018 by the United States Patent and Trademark Office in U.S. Appl. No. 14/961,145.
Final Office Action dated Mar. 8, 2018 by the United States Patent and Trademark Office in U.S. Appl. No. 14/844,437.
Restriction Requirement dated Mar. 8, 2018 by the United States Patent and Trademark Office in U.S. Appl. No. 14/833,221.
Non-Final Office Action dated Jan. 30, 2018 by the United States Patent and Trademark Office in U.S. Appl. No. 15/068,760.
Non-Final OA dated Aug. 24, 2017 issued by the United States Patent and Trademark Office in U.S. Appl. No. 14/844,437.
Non-Final Office Action dated Sep. 27, 2017 issued by the United States Patent and Trademark Office in U.S. Appl. No. 14/961,145.
Non-Final Office Action dated Nov. 1, 2017 issued by the United States Patent and Trademark Office in U.S. Appl. No. 14/862,288.
Final OA dated Sep. 26, 2017 issued by the United States Patent and Trademark Office in U.S. Appl. No. 15/068,760.
Restriction Requirement dated Jan. 14, 2019 issued by the United States Patent and Trademark Office in U.S. Appl. No. 15/654,422.
Non-Final Office dated Dec. 14, 2018 issued by the United States Patent and Trademark Office in U.S. Appl. No. 14/884,019.
Advisory Action dated Dec. 19, 2017 issued by the United States Patent and Trademark Office in U.S. Appl. No. 15/068,760.
Anonymous, ""Central Venous Pressure Waveforms"", Section 3: Anesthesia Management, Part B: Monitoring, Chapter 30: Cardiovascular Monitoring, 1979, http://web.squ.edu.om/med-Lib/MED_CD/E_CDs/anesthesia/site/content/v03/030275r00.HTM; 4 pages total.
Office Action dated Feb. 15, 2019 issued by the U.S. Patent and Trademark Office in U.S. Appl. No. 14/961,145.
Final Office Action dated Mar. 7, 2019 issued by the USPTO in counterpart U.S. Appl. No. 14/833,221.
Notice of Allowance dated Mar. 18, 2019 issued by the USPTO in counterpart U.S. Appl. No. 15/068,760.
Non-Final Office Action dated Mar. 22, 2019 issued by the USPTO in counterpart U.S. Appl. No. 14/862,288.
Notice of Allowance dated Apr. 24, 2019, issued by the USPTO in counterpart Appl. No. 14/961,145.
Non-Final Office Action dated Apr. 26, 2019 issued by the USPTO in counterpart U.S. Appl. No. 15/654,422.

* cited by examiner

DIRECTION a

# APPARATUS FOR DETECTING BIO-INFORMATION

CROSS-REFERENCE TO RELATED APPLICATION

This application claims priority from Korean Patent Application No. 10-2015-0007445, filed on Jan. 15, 2015, in the Korean Intellectual Property Office, the disclosure of which is incorporated herein by reference in its entirety.

BACKGROUND

1. Field

Apparatuses and methods consistent with exemplary embodiments relate to an apparatus for detecting bio-information and a method thereof.

2. Description of the Related Art

Along with an increased interest in health, various types of apparatuses for detecting bio-information have been developed. Particularly, along with the spread of various wearable devices directly wearable by an object, devices for healthcare have been developed.

Methods of detecting bio-information such as a pulse wave may be largely classified into invasive methods and noninvasive methods, and the noninvasive methods capable of simply detecting a pulse wave without causing pain to an object are usually used.

For accurate pulse wave analysis (PWA), information based on an optical signal or a pressure signal needs to be obtained from a certain body surface of an object. Bio-information of the object may be obtained based on the information, and various methods are used to reduce measurement errors.

SUMMARY

Exemplary embodiments address at least the above problems and/or disadvantages and other disadvantages not described above. Also, the exemplary embodiments are not required to overcome the disadvantages described above, and may not overcome any of the problems described above.

Exemplary embodiments provide bio-information detection apparatuses capable of acquiring bio-information by detecting a bio-signal based on an optical signal, and methods thereof.

According to an aspect of an exemplary embodiment, there is provided an apparatus for detecting bio-information including a bio-signal detector including a light emitter including a light-emitting diode (LED) and a laser diode (LD), the LED and the LD being configured to emit optical signals on an object. The bio-signal detector further includes an optical detector including a light-receiver configured to detect optical signals modulated by the object. The apparatus further includes a processor configured to process the optical signals to detect the bio-information of the object.

The optical detector may include light-receivers disposed to surround the light emitter, the light receivers being configured to detect the optical signals modulated by the object.

The light-receivers may be disposed at four or more points surrounding the light emitter.

The light-receivers may be disposed in a shape of a ring surrounding the light emitter.

The light emitter may include LEDs and LDs, the LEDs and the LDs being disposed in a two-dimensional array, and the LEDs and the LDs being configured to emit the optical signals on the object.

The optical detector may include light-receivers configured to detect the optical signals modulated by the object, and the light emitter may include LEDs and LDs, the LEDs and the LDs being configured to emit the optical signals on the object. The LEDs and the LDs may be disposed in a line, and the light-receivers may be disposed in an array along a side of the line of the LEDs and the LDs.

The bio-signal detector may have a structure in which sub-units are repeatedly disposed, each of the sub-units including one light emitter configured to emit optical signals on the object, and light-receivers disposed to surround the one light emitter, the light receivers being configured to detect the optical signals modulated by the object.

The apparatus may be wearable by the object.

The LED and the LD may be further configured to emit the optical signals with a delay time.

The LED and the LD may be further configured to emit the optical signals at a same time.

The LED and the LD may be disposed at a same distance from a surface of the object or the apparatus.

The LD may be disposed at a distance from a surface of the object or the apparatus that is farther than a distance at which the LED is disposed from the surface.

The optical signals may include photoplethysmogram signals or pulse waves of a surface of skin of the object.

The bio-information may be at least one among a blood oxygen saturation level, a blood pressure, a vascular compliance, a blood flow rate, and a degree of arteriosclerosis.

According to an aspect of another exemplary embodiment, there is provided a method of detecting bio-information, the method including driving a light-emitting diode (LED) and a laser diode (LD) with a delay time to irradiate lights having different divergent angles on an object with the delay time, and detecting signals reflected by the object, the signals having the delay time. The method further includes selecting a signal having a signal-to-noise ratio greater than a value from the detected signals, or combining the detected signals, to detect the bio-information of the object.

The detected signals may be photoplethysmogram (PPG) signals or pulse waves of a surface of skin of the object, and the method may further include processing the PPG signals or the pulse waves to detect the bio-information.

According to an aspect of another exemplary embodiment, there is provided an apparatus configured to detect bio-information, the apparatus including a light-emitting diode (LED) and a laser diode (LD) configured to emit lights having different divergent angles on an object, light-receivers configured to detect signals reflected by the object, and a processor configured to process the signals to detect the bio-information of the object.

BRIEF DESCRIPTION OF THE DRAWINGS

The above and/or other aspects will be more apparent by describing certain exemplary embodiments with reference to the accompanying drawings in which.

DETAILED DESCRIPTION OF THE EXEMPLARY EMBODIMENTS

Figure 1:
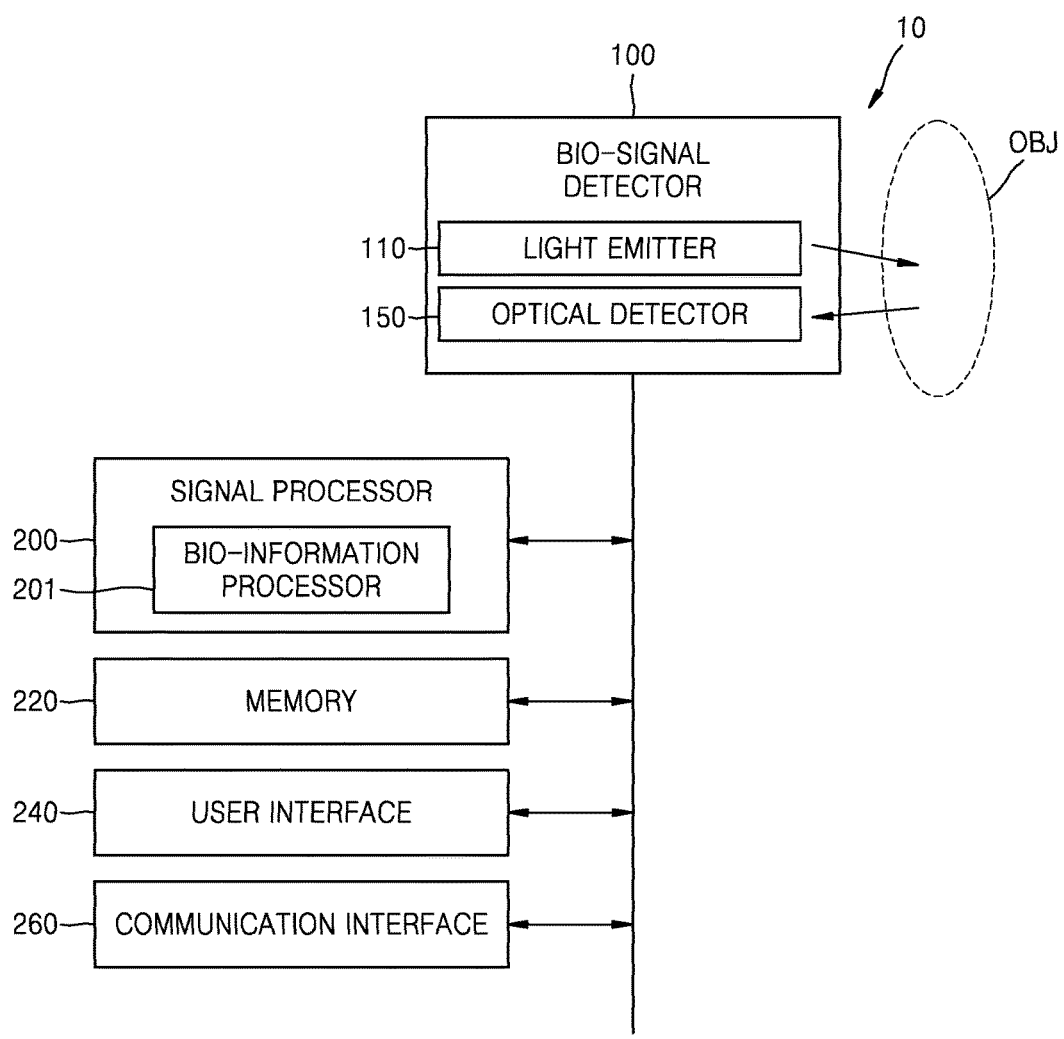
FIG. 1 is a block diagram of an apparatus for detecting bio-information, according to an exemplary embodiment.

Exemplary embodiments are described in greater detail herein with reference to the accompanying drawings.

In the following description, like drawing reference numerals are used for like elements, even in different drawings. The matters defined in the description, such as detailed construction and elements, are provided to assist in a comprehensive understanding of the exemplary embodiments. However, it is apparent that the exemplary embodiments can be practiced without those specifically defined matters. Also, well-known functions or constructions are not described in detail since they would obscure the description with unnecessary detail.

Hereinafter, when it is described that a component is "above" or "on" another component, the component may be directly above the other component, or a third component may be interposed therebetween.

Although terms, such as 'first' and 'second,' can be used to describe various elements, the elements cannot be limited by the terms. The terms can be used to classify an element from another element.

An expression in the singular includes an expression in the plural unless they are clearly different from each other in context. In addition, when a part "includes" a component, this indicates that the part may further include another component instead of excluding another component unless there is different disclosure.

In addition, the terms such as "unit," "-er (-or)," and "module" described in the specification refer to an element for performing at least one function or operation, and may be implemented in hardware, software, or a combination of hardware and software.

As used herein, the term "and/or" includes any and all combinations of one or more of associated listed items. Expressions such as "at least one of," when preceding a list of elements, modify the entire list of elements and do not modify the individual elements of the list.

FIG. 1 is a block diagram of an apparatus 10 for detecting bio-information, according to an exemplary embodiment.

Referring to FIG. 1, the apparatus 10 detects bio-information of an object OBJ. The apparatus 10 includes a bio-signal detector 100 and a signal processor 200 for analyzing the bio-information by using a measurement result of the bio-signal detector 100. The apparatus 10 further includes a memory 220, a user interface 240, and a communication interface 260.

The bio-signal detector 100 includes a light emitter 110 and an optical detector 150. The light emitter 110 of the bio-signal detector 100 includes at least one light-emitting diode (LED) and at least one laser diode (LD). The optical detector 150 of the bio-signal detector 100 is disposed around the light emitter 110 and includes at least one light-receiver. A photodiode, a photo transistor (PTr), a charge-coupled device (CCD), or the like may be used as the light-receiver. The light-receiver detects optical signals scattered and reflected from the object OBJ.

The bio-signal detector 100 generates lights from the LED and the LD, irradiates the generated lights on the object OBJ, and detects lights modulated by the object OBJ, e.g., lights scattered and reflected from the object OBJ, by using the light-receiver. In this case, the LED and the LD may be driven to generate optical signals with a delay time or to simultaneously generate the optical signals by being turned on at the same time.

The optical signals detected by the optical detector 150 of the bio-signal detector 100, e.g., photoplethysmogram (PPG) signals or skin surface pulse waves, are transmitted to the signal processor 200. When the LED and the LD are driven to generate optical signals with a delay time, the optical detector 150 of the bio-signal detector 100 may detect the optical signals with the delay time. Various exemplary embodiments of the bio-signal detector 100 will be described below. Herein, the PPG signal is a signal obtained by detecting modulated light varying according to a change in a blood volume inside the skin, and because the modulated light is reflected a small amount for a large amount of blood and is reflect a large amount for a small amount of blood, the detected PPG signal varies according to the blood volume. The skin surface pulse wave is a signal obtained by detecting a change in reflected light detected by the optical detector 150 due to vibrations on a skin surface. Vibrations on the skin surface occur according to a change in a blood volume in a blood vessel, and the skin vibrations change a traveling direction of light reflected from the skin surface. Therefore, when skin vibrations occur according to a blood volume, an intensity of light incident to the optical detector 150 varies, and thus the skin surface pulse wave, which is an optical signal detected by the optical detector 150, also varies.

The object OBJ may be a living body part, which may be in contact with or adjacent to the bio-signal detector 100 of the apparatus 10, or a human body part of which a pulse wave may be measured through photoplethysmography. For example, the object OBJ may be a region of a wrist surface that is adjacent to a radial artery. When a pulse wave is measured from a skin surface of a wrist inside which the radial artery passes, influences of external causes causing measurement errors, such as a thickness of skin tissue inside the wrist and the like, may be relatively small. The radial artery corresponds to a blood vessel from which accurate blood pressure may be measured, compared with other types of blood vessels inside the wrist. However, the object OBJ is not limited to a radial artery and may be another peripheral part such as a finger, a toe, an ear lobe, or the like, which is a part having a high blood vessel density in a human body.

The signal processor 200 includes a bio-information processor 201. In addition, the signal processor 200 may further include a pulse wave processor.

The pulse wave processor may analyze a per-time intensity change of an optical signal detected by the optical detector 150. The pulse wave processor may acquire a bio-signal by analyzing fluctuation of an optical signal corresponding to a volume change of a blood vessel (e.g., the radial artery) of the object OBJ. The acquired bio-signal may be a PPG signal converted based on a correlation between the analyzed fluctuation of the optical signal and the volume change. The pulse wave processor may analyze various parameters included in a PPG pulse wave signal by analyzing waveform characteristics of the PPG pulse wave signal. For example, the pulse wave processor may calculate a delay time between pulse wave signals and calculate a pulse transit time (PPT) from the calculated delay time. In this process, various digital signal processing algorithms such as a noise cancellation algorithm, a differential signal extraction algorithm, and the like may be used.

The bio-information processor 201 may analyze various pieces of bio-information by using the pulse wave signal analysis result as an index. The bio-information processor 201 may analyze the bio-information by using a predetermined algorithm of calculating various pieces of bio-information from the PPT analyzed by the pulse wave processor. For example, the bio-information processor 201 may estimate a vascular compliance, a blood flow rate, a degree of arteriosclerosis, a systolic or diastolic blood pressure of a blood vessel, a blood oxygen saturation level, and the like.

The memory 220 may store programs for processing and controlling of the signal processor 200 and store input/output data. For example, programs for the pulse wave analysis and the bio-information analysis performed by the signal processor 200 may be stored in the memory 220 as code. In addition, measurement results of the bio-signal detector 100, which are for processing of the signal processor 200, may be stored in the memory 220. The memory 220 may include at least one type of storage medium among a flash memory type memory, a hard disk type memory, a multimedia card micro type memory, a card type memory (e.g., a secure digital (SD) or extreme digital (XD) memory or the like), random access memory (RAM), static RAM (SRAM), read only memory (ROM), electrically erasable programmable ROM (EEPROM), PROM, a magnetic memory, a magnetic disc, and an optical disc.

The user interface 240 is an interface that interfaces with a user and/or an external device and may include an input module and an output module. The user may be a target of which bio-information is to be measured, i.e., the object OBJ, or may have a wider concept than the object OBJ, i.e., may be a person who may use the apparatus 10, such as a medical expert or the like. Through the user interface 240, information to be used to operate the apparatus 10 may be inputted, and an analysis result may be outputted. The user interface 240 may include, for example, a button, a connector, a keypad, a display, and the like and may further include components such as a speaker, a vibration motor, and the like.

The communication interface 260 may transmit an analysis result to an external device. The external device may be medical equipment using analyzed bio-information, a printer for printing a result, or a display device for displaying an analysis result. Also, the external device may be one of various devices such as a smartphone, a cellular phone, a personal digital assistant (PDA), a laptop computer, a PC, and other mobile or non-mobile computing devices.

The communication interface 260 may be connected to the external device in a wired or wireless manner. For example, the communication interface 260 may communicate with the external device by using various communication schemes such as Bluetooth, Bluetooth low energy (BLE), near-field communication (NFC), wireless local area network (WLAN), ZigBee, infrared data association (IrDA), Wi-Fi Direct (WFD), ultra wideband (UWB), Ant+, Wi-Fi, and the like.

The apparatus 10 may be implemented in a type of a device wearable by the object OBJ, i.e., a wearable device type. For example, the apparatus 10 may be implemented in various types such as a watch type, a bracelet type, a wrist band type, a ring type, an eyeglass type, a hairband type, and the like. Alternatively, only a partial component of the apparatus 10, e.g., the bio-signal detector 100, may be implemented in a type of a device wearable by the object OBJ.

Various exemplary embodiments of the bio-signal detector 100, which may be employed in the apparatus 10 of FIG. 1, will now be described in detail.

Figure 2:
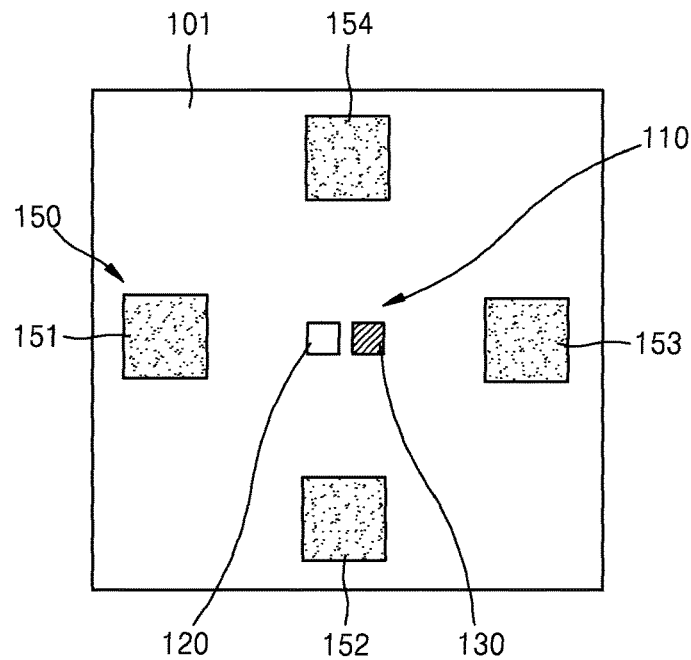
FIG. 2 is a diagram of a bio-signal detector employed in the apparatus of FIG. 1, according to an exemplary embodiment.
Figure 3:
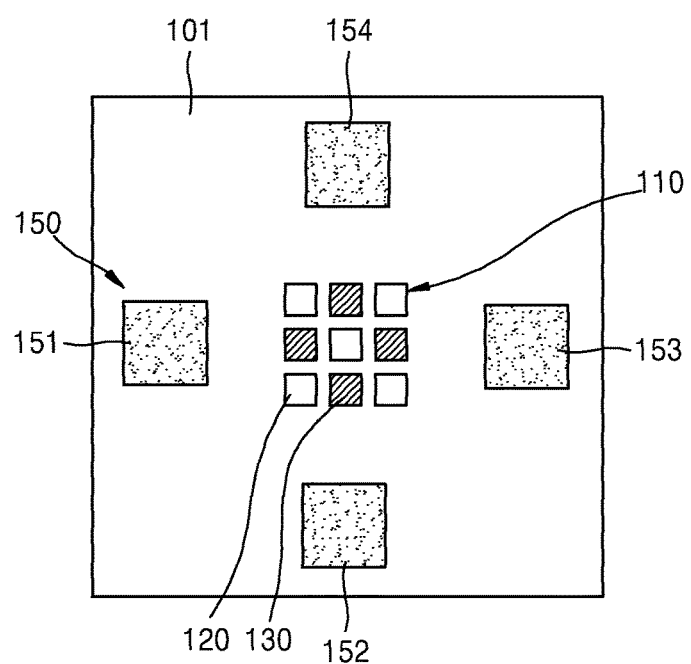
FIG. 3 is a diagram of the bio-signal detector employed in the apparatus of FIG. 1, according to another exemplary embodiment.

FIG. 2 is a diagram of the bio-signal detector 100 employed in the apparatus 10 of FIG. 1, according to an exemplary embodiment, and FIG. 3 is a diagram of the bio-signal detector 100 employed in the apparatus 10 of FIG. 1, according to another exemplary embodiment.

The light emitter 110 may include, for example, one LED 120 and one LD 130, as shown in FIG. 2.

As another example, the light emitter 210 may include, for example, a plurality of LEDs 120 and a plurality of LDs 130, as shown in FIG. 3. The plurality of LEDs 120 and the plurality of LDs 130 may be arranged in combination to form a two-dimensional array. FIG. 3 shows a case where the LEDs 120 and the LDs 130 are alternately located one by one, but this is only illustrative, and a predetermined number of LEDs 120 and a predetermined number of LDs 130 may be alternately located, or the LEDs 120 and the LDs 130 may be irregularly located.

Referring to FIGS. 2 and 3, the optical detector 150 may include a plurality of light-receivers 151 to 154 to increase a light-receiving ratio of light modulated by the object OBJ. The plurality of light-receivers 151 to 154 are arranged around the light emitter 110.

For example, the plurality of light-receivers 151 to 154 may be arranged at four or more points around the light emitter 110. FIGS. 2 and 3 illustrate a case where the plurality of light-receivers 151 to 154 is arranged at four points around the light emitter 110.

In FIGS. 2 and 3, reference numeral 101 indicates a substrate on which the light emitter 110 and the optical detector 150 are disposed, e.g., a printed circuit board (PCB).

Figure 4:
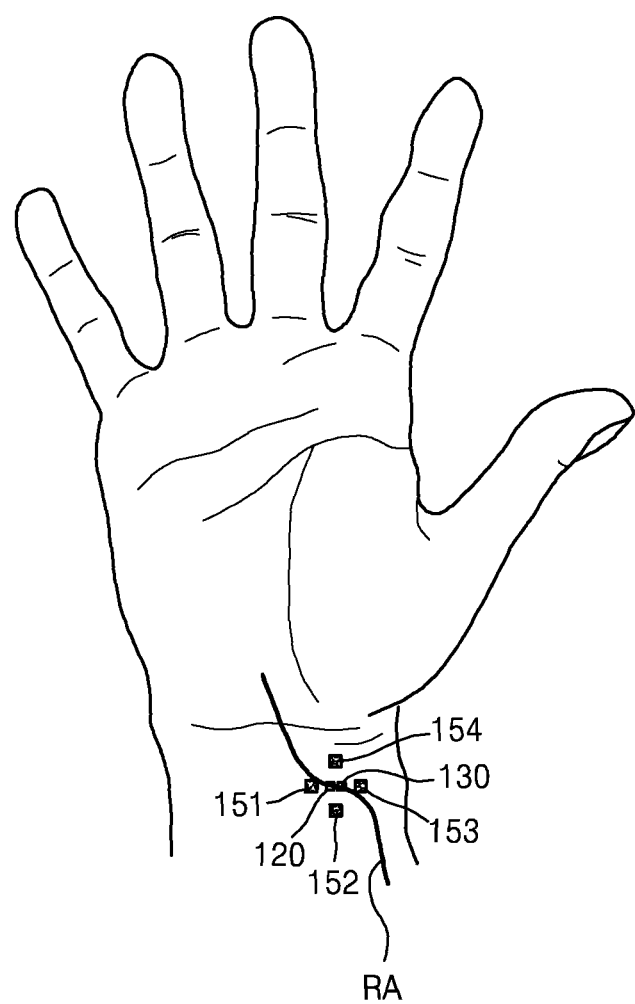
FIG. 4 is a diagram of the bio-signal detector of FIG. 2 that is located on a radial artery to measure bio-information.

As described above, when the bio-signal detector 100 having a structure in which the plurality of light-receivers 151 to 154 are arranged at four or more points around the light emitter 110 is used, bio-information may be obtained by measuring a bio-signal, for example, as shown in FIG. 4.

FIG. 4 is a diagram of the bio-signal detector 100 of FIG. 2 that is located on a radial artery RA to measure bio-information.

Figure 5:
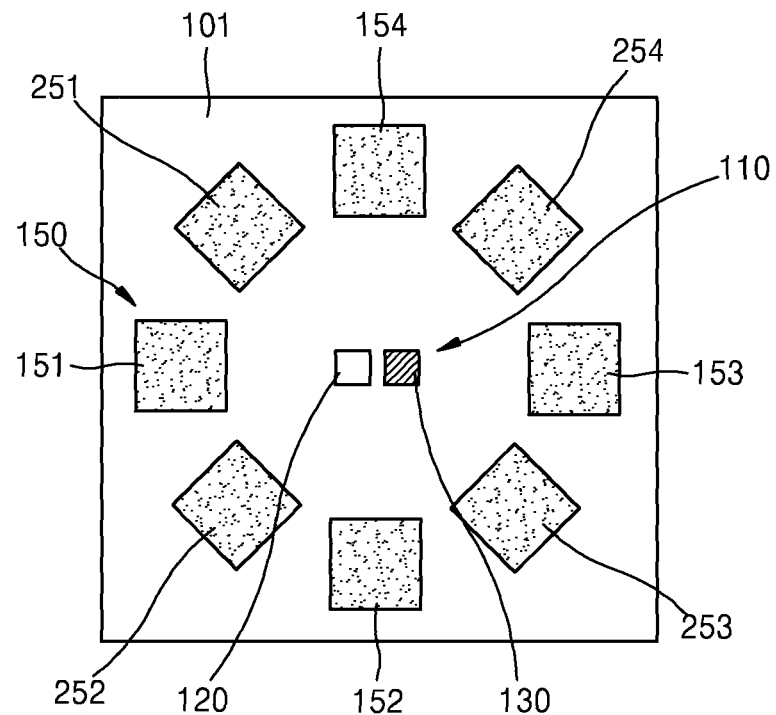
FIGS. 5 and 6 are diagrams of the bio-signal detector employed in the apparatus of FIG. 1, according to other exemplary embodiments.
Figure 6:
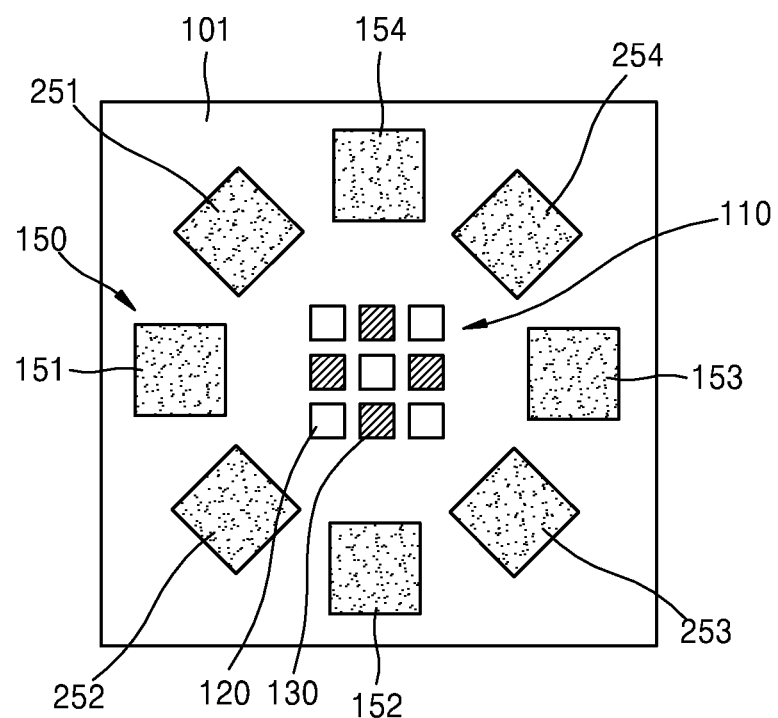

FIGS. 5 and 6 are diagrams of the bio-signal detector 100 employed in the apparatus 10 of FIG. 1, according to other exemplary embodiments. FIGS. 5 and 6 show cases where the light emitter 110 has the structures of FIGS. 2 and 3, respectively, and the optical detector 150 is disposed such that the plurality of light-receivers 151 to 154 and a plurality of light-receivers 251 to 254 form a ring shape around the light emitter 110.

The light emitter 110 may include the LED 120 and the LD 130, as shown in FIG. 5. Alternatively, the light emitter 110 may include the plurality of LEDs 120 and the plurality of LDs 130, as shown in FIG. 6, and the plurality of LEDs 120 and the plurality of LDs 130 may be arranged in combination to form a two-dimensional array.

Figure 7:
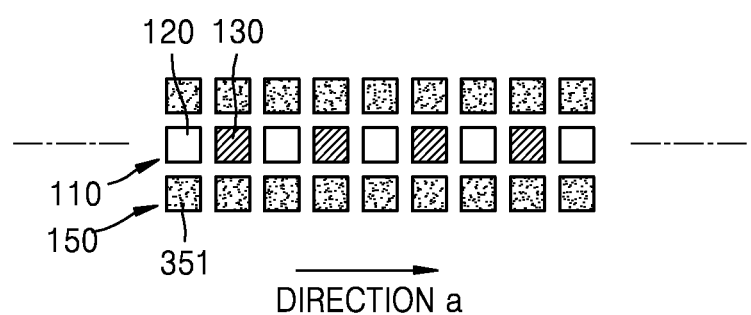
FIGS. 7 and 8 are diagrams of the bio-signal detector employed in the apparatus of FIG. 1, according to other exemplary embodiments.
Figure 8:
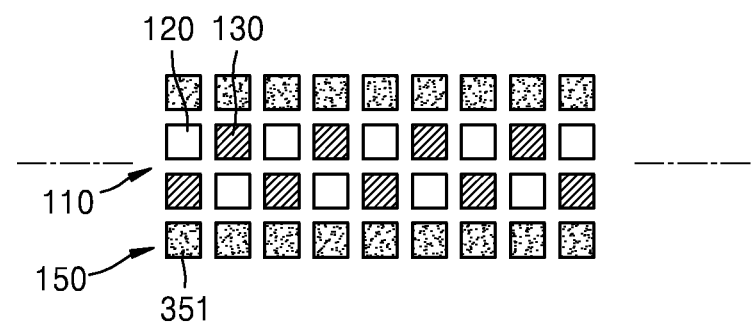
Figure 9:
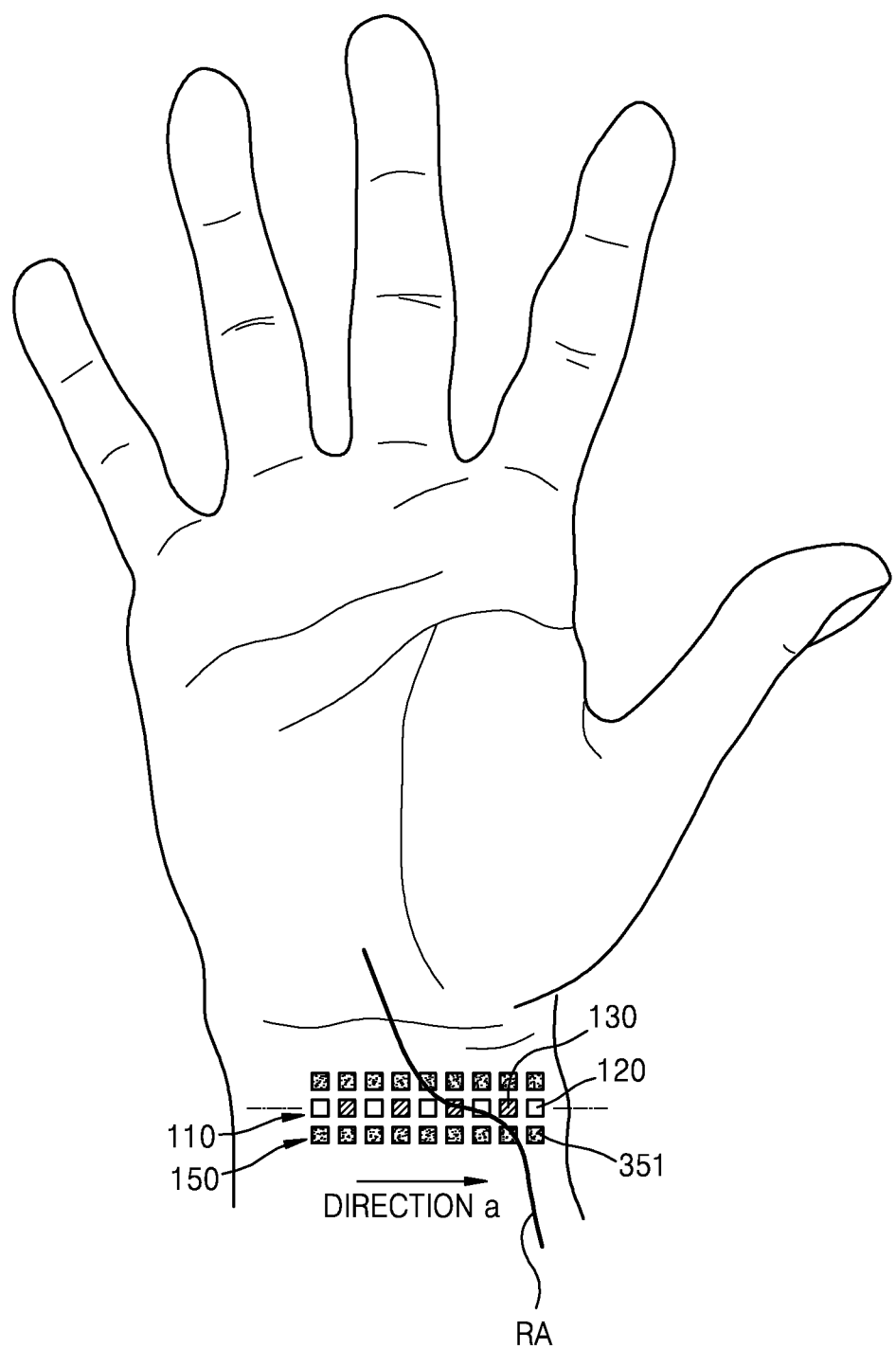
FIG. 9 is a diagram of the bio-signal detector of FIG. 7 that is located on a radial artery to measure bio-information.

FIGS. 7 and 8 are diagrams of the bio-signal detector 100 employed in the apparatus 10 of FIG. 1, according to other exemplary embodiments. FIG. 9 is a diagram of the bio-signal detector 100 of FIG. 7 that is located on a radial artery to measure bio-information.

Referring to FIGS. 7 and 8, the light emitter 110 may include the plurality of LEDs 120 and the plurality of LDs 130, and the optical detector 150 may include a plurality of light-receivers 351. The plurality of LEDs 120 and the plurality of LDs 130 may be linearly arranged in combination to form one or more lines, and the plurality of light-receivers 351 may be arranged to form an array along at least one side of the linear arrangement of the plurality of LEDs 120 and the plurality of LDs 130.

FIG. 7 shows a case where the light emitter 110 has a structure in which the plurality of LEDs 120 and the plurality of LDs 130 are linearly arranged in combination to form one line, and the optical detector 150 has a structure in which the plurality of light-receivers 351 are arranged to form arrays along both sides of the linear arrangement of the plurality of LEDs 120 and the plurality of LDs 130.

FIG. 8 shows a case where the light emitter 110 has a structure in which the plurality of LEDs 120 and the plurality of LDs 130 are linearly arranged in combination to form two lines, and the optical detector 150 has a structure in which the plurality of light-receivers 351 are arranged to form arrays along both sides of the linear arrangement of the plurality of LEDs 120 and the plurality of LDs 130.

As shown in FIGS. 7 and 8, when the light emitter 110 and the optical detector 150 are configured to have the linear arrangement of a plurality of optical elements, the bio-signal detector 100 may be implemented as a wearable device and worn around a wrist or the like, as shown in FIG. 9.

Referring to FIG. 9, even when the wearable device is worn, for example, in a direction a, the LEDs 120, the LDs 130, and the light-receivers 351 may be located on and nearby a radial artery RA, and thus a bio-signal may be smoothly detected.

Figure 10:
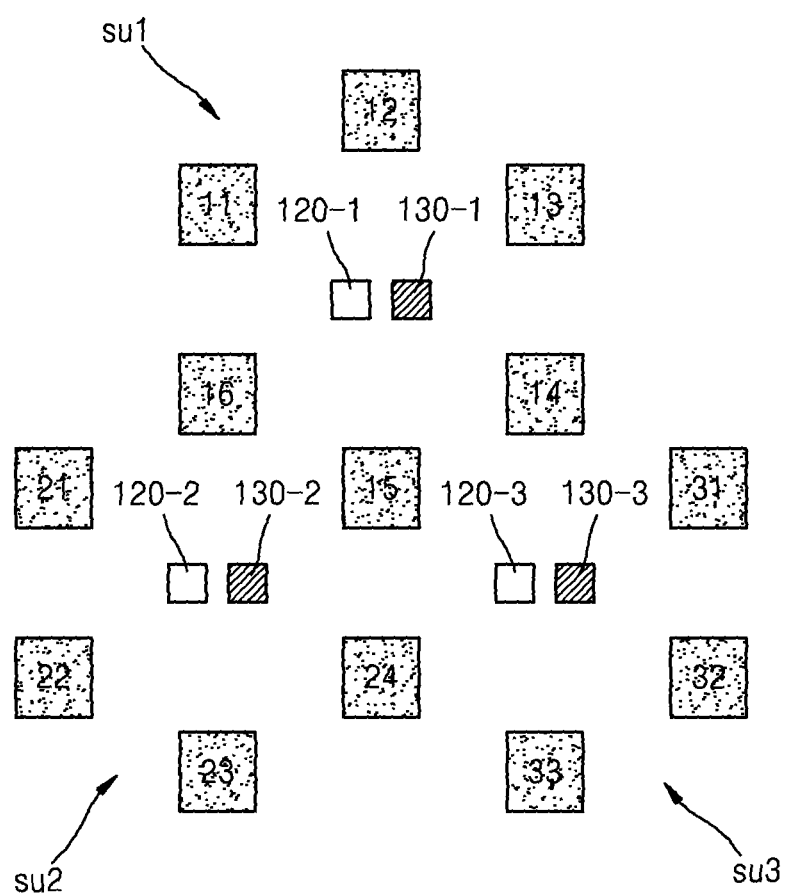
FIG. 10 is a diagram of a bio-signal detector employed in the apparatus of FIG. 1, according to another exemplary embodiment.

FIG. 10 is a diagram of the bio-signal detector 100 employed in the apparatus 10 of FIG. 1, according to another exemplary embodiment.

Referring to FIG. 10, the bio-signal detector 100 may have a structure in which a light emitter and an optical detector including a plurality of light-receivers surrounding the light emitter form one sub-unit, and a plurality of sub-units are repeatedly arranged.

For example, a first light emitter, including an LED 120-1 and an LD 130-1, and a plurality of light-receivers 11 to 16 surrounding the first light emitter may form a first sub-unit SU1, a second light emitter, including an LED 120-2 and an LD 130-2, and a plurality of light-receivers 21 to 24, 15, and 16 surrounding the second light emitter may form a second sub-unit SU2, and a third light emitter, including an LED 120-3 and an LD 130-3, and a plurality of light-receivers 31 to 33, 24, 15, and 14 surrounding the third light emitter may form a third sub-unit SU3.

In one sub-unit, a light-receiver may detect an optical signal modulated by the object OBJ while driving an LED and an LD included in the one sub-unit, and the optical signal, e.g., a bio-signal level, may be identified and stored. An optimal bio-signal may be selected by repeating a measurement for a plurality of sub-units and comparing stored bio-signal levels.

FIG. 10 illustrates a case where each light emitter includes one LED and one LD. However, at least one of a plurality of light emitters may have the structure as described with reference to FIG. 3 in which the plurality of LEDs 120 and the plurality of LDs 130 are arranged in combination to form a two-dimensional array.

In addition, FIG. 10 shows a case where the bio-signal detector 100 includes three sub-units, but this is only illustrative, and the bio-signal detector 100 may include three or more sub-units.

Figure 11:
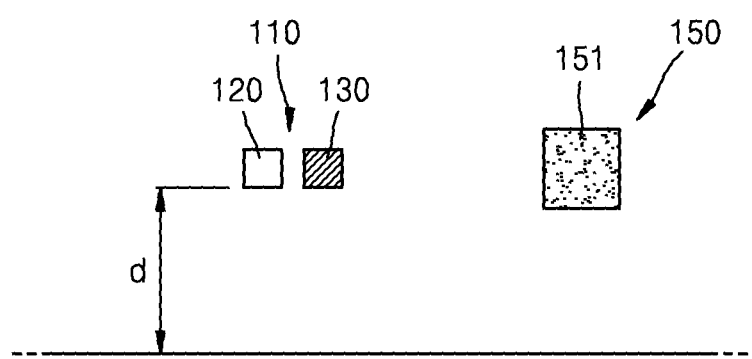
FIGS. 11 and 12 are diagrams illustrating relative location relationships between a light-emitting diode (LED) and a laser diode (LD), according to exemplary embodiments.
Figure 12:
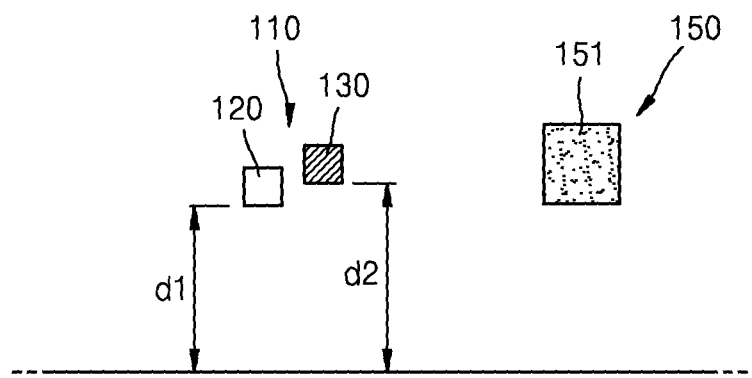

FIGS. 11 and 12 are diagrams illustrating relative location relationships between an LED and an LD, according to exemplary embodiments.

In the bio-signal detector 100 according to the various exemplary embodiments described above, the LED 120 and the LD 130 of the light emitter 110 may be located at a same distance d from a reference surface, as shown in FIG. 11.

Alternatively, in the bio-signal detector 100 according to the various exemplary embodiments described above, the LED 120 and the LD 130 of the light emitter 110 may be located at different distances d1 and d2, respectively, from the reference surface, as shown in FIG. 12.

The reference surface may be, for example, a predetermined location, e.g., a surface of a wrist where a radial artery is located, of the object OBJ wearing a wearable device when the apparatus 10 is implemented as the wearable device, or a predetermined location of the apparatus 10.

Output light of the LED 120 is diverged, and output light of the LD 130 is relatively not diverged. Therefore, when the LED 120 is used, if the LED 120 is spaced apart by a predetermined distance from a part to be measured, a bio-signal, e.g., a PPG signal, may not be accurately measured. In addition, when the LD 130 is used, on the contrary, if the LD 130 is too close to a part to be measured, a bio-signal, e.g., a PPG signal, may not be accurately measured.

In consideration of the description above, the light emitter 110 of the bio-signal detector 100 may include the LED 120 and the LD 130 such that the LED 120 and the LD 130 are located at the different distances d1 and d2, respectively, from the reference surface, as shown in FIG. 12. In this example, the LED 120 and the LD 130 may be arranged such that the LD 130 is farther from the reference surface than the LED 120, i.e., d2>d1.

The arrangement of the LED 120 and the LD 130 of the light emitter 110 such that the LED 120 and the LD 130 are located at the same distance d from the reference surface, as shown in FIG. 11, or located at the different distances d1 and d2, respectively, from the reference surface, as shown in FIG. 12, may be applied to FIGS. 2, 3, 5, 6, 7, 8, and 10. Also, for FIGS. 3, 6, 7, 8, and 10, in which the plurality of LEDs 110 and the plurality of LDs 130 are included, a case where the LED 120 and the LD 130 are located at the same distance d from the reference surface, and a case where the LED 120 and the LD 130 are located at the different distances d1 and d2, respectively, from the reference surface, may be arranged in combination.

As described above, in the bio-signal detector 100 according to various exemplary embodiments, a light emitter is configured to include at least one LED and at least one LD, the LED and the LD generate optical signals, and a bio-signal is measured by detecting optical signals modulated by an object OBJ through a plurality of light-receivers.

The bio-signal detector 100 according to the various exemplary embodiments measures the bio-signal for the object OBJ, e.g., a PPG signal or a skin surface pulse wave, and the bio-information processor 201 of the signal processor 200 analyzes bio-information of the object OBJ from the bio-signal. The bio-information may be a blood oxygen saturation level or blood pressure, or may correspond to various pieces of bio-information that may be obtained using the PPG signal or the skin surface pulse wave, e.g., a vascular compliance, a blood flow rate, and a degree of arteriosclerosis.

According to the apparatus 10 according to the above exemplary embodiments, light sources having different characteristics, i.e., the LED and the LD, are arranged in combination at one location, and lights having different divergent angles are irradiated on the object OBJ with a delay time by, for example, driving the LED and the LD with the delay time. Accordingly, a light-receiver arranged around the LED and the LD obtains optical signals modulated by the object OBJ, e.g., PPG signals or skin surface pulse waves, with the delay time. That is, the light-receiver arranged around the LED and the LD detects optical signals having the delay time according to the time-delayed driving of the LED and the LD. The detected optical signals, e.g., the PPG signals or the skin surface pulse waves, are transmitted to the signal processor 200, and the signal processor 200 performs bio-information analysis, e.g., PPG analysis, by selecting a signal having a good signal-to-noise ratio (i.e., greater than a predetermined value) from the detected signals or combining two of the detected signals, and obtains desired bio-information.

Also, according to the apparatus 10 according to the above exemplary embodiments, the light sources having different characteristics, i.e., the LED and the LD, are arranged in combination at one location, and the lights having different divergent angles are irradiated on the object OBJ at the same time by, for example, simultaneously driving the LED and the LD. Accordingly, a light-receiver arranged around the LED and the LD obtains optical signals modulated by the object OBJ, e.g., PPG signals or skin surface pulse waves. That is, the light-receiver arranged around the LED and the LD detects optical signals according to the simultaneous driving of the LED and the LD. The detected optical signals, e.g., the PPG signals or the skin surface pulse waves, are transmitted to the signal processor 200, and the signal processor 200 performs bio-information analysis, e.g., PPG analysis, by selecting a signal having a good signal-to-noise ratio from the detected signals or combining the two signals, and obtains desired bio-information.

In this case, the signals detected by the apparatus 10 may be, for example, the PPG signals or skin surface pulse waves for the object OBJ, and the bio-information is analyzed from the PPG signals or the skin surface pulse waves. The analyzed bio-information may be a blood oxygen saturation level or blood pressure, or may correspond to various pieces of bio-information, which may be obtained using the PPG signals or the skin surface pulse waves, e.g., a vascular compliance, a blood flow rate, and a degree of arteriosclerosis. That is, the apparatus 10 may be used in devices for analyzing a PPG signal or a skin surface pulse wave, e.g., devices for analyzing blood pressure or a pulse wave. For example, the apparatus 10 may be applied to medical diagnosis devices, e.g., a device for measuring blood pressure, and a device for measuring an oxygen saturation level.

As described above, according to the above exemplary embodiments, an apparatus for detecting bio-information may acquire bio-information by detecting a bio-signal based on an optical signal. In addition, an LED and an LD are combined as light sources, and because bio-signals by the LED and the LD, e.g., PPG signals or skin surface pulse waves, may be obtained, various types of bio-signals according to optical characteristics, e.g., PPG signals or skin surface pulse waves, may be obtained, and thus the bio-signals may be accurately measured.

In addition, the exemplary embodiments may also be implemented through computer-readable code and/or instructions on a medium, e.g., a non-transitory computer-readable medium, to control at least one processing element to implement any above-described embodiments. The medium may correspond to any medium or media which may serve as a storage and/or perform transmission of the computer-readable code.

The computer-readable code may be recorded and/or transferred on a medium in a variety of ways, and examples of the medium include recording media, such as magnetic storage media (e.g., ROM, floppy disks, hard disks, etc.) and optical recording media (e.g., compact disc read only memories (CD-ROMs) or digital versatile discs (DVDs)), and transmission media such as Internet transmission media. Thus, the medium may have a structure suitable for storing or carrying a signal or information, such as a device carrying a bitstream according to one or more exemplary embodiments. The medium may also be on a distributed network, so that the computer-readable code is stored and/or transferred on the medium and executed in a distributed fashion. Furthermore, the processing element may include a processor or a computer processor, and the processing element may be distributed and/or included in a single device.

The foregoing exemplary embodiments and advantages are merely exemplary and are not to be construed as limiting. The present teaching can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. An apparatus configured to detect bio-information, the apparatus comprising:
   a bio-signal detector comprising:
      a light emitter comprising a plurality of light-emitting diodes (LEDs) and a plurality of laser diodes (LDs), the plurality of LEDs and the plurality of LDs being disposed in a two-dimensional array and configured to emit optical signals on an object; and
      an optical detector comprising a plurality of light-receivers disposed to surround the plurality of LEDs and the plurality of LDs, the optical detector being configured to detect the optical signals that are modulated by the object; and
   a processor configured to process the optical signals to detect the bio-information of the object.

2. The apparatus of claim 1, wherein the plurality of light-receivers are disposed at four or more points surrounding the light emitter.

3. The apparatus of claim 1, wherein the plurality of light-receivers are disposed in a shape of a ring surrounding the light emitter.

4. The apparatus of claim 1, wherein the plurality of LEDs and the plurality of LDs are disposed in a line, and
   wherein the plurality of light-receivers are disposed in an array along a side of the line of the plurality of LEDs and the plurality of LDs.

5. The apparatus of claim 1, wherein the apparatus is wearable by the object.

6. The apparatus of claim 1, wherein the plurality of LEDs and the plurality of LDs are further configured to emit the optical signals with a delay time.

7. The apparatus of claim 1, wherein the plurality of LEDs and the plurality of LDs are further configured to emit the optical signals at a same time.

8. The apparatus of claim 1, wherein a first optical signal that is emitted from the plurality of LEDs has a first divergent angle different than a second divergent angle of a second optical signal that is emitted from the plurality of LDs.

9. The apparatus of claim 1, wherein the plurality of LEDs and the plurality of LDs are disposed at a same distance from a reference surface or the plurality of LDs is disposed at a first distance from the reference surface that is farther than a second distance at which the plurality of LEDs is disposed from the reference surface, and
wherein the reference surface is to the object or the apparatus.

10. The apparatus of claim 1, wherein the optical signals comprise photoplethysmogram signals or pulse waves of a surface of skin of the object.

11. The apparatus of claim 1, wherein the bio-information is at least one among a blood oxygen saturation level, a blood pressure, a vascular compliance, a blood flow rate, and a degree of arteriosclerosis.

12. A method of detecting bio-information, the method comprising:
driving a plurality of light-emitting diodes (LEDs) and a plurality of laser diodes (LDs) with a delay time to irradiate lights having different divergent angles on an object with the delay time, the plurality of LEDs and the plurality of LDs being disposed in a two-dimensional array;
detecting signals that are reflected and modulated by the object, the signals having the delay time, and the signals being detected by an optical detector comprising a plurality of light-receivers disposed to surround the plurality of LEDs and the plurality of LDs; and
selecting, by a processor, a signal having a signal-to-noise ratio greater than a value from the signals that are detected, or combining the signals that are detected, to detect the bio-information of the object.

13. The method of claim 12, wherein the signals are photoplethysmogram (PPG) signals or pulse waves of a surface of skin of the object, and
wherein the method further comprises processing the PPG signals or the pulse waves to detect the bio-information.

14. The method of claim 12, wherein the bio-information is at least one among a blood oxygen saturation level, a blood pressure, a vascular compliance, a blood flow rate, and a degree of arteriosclerosis.

15. The method of claim 12, wherein one of the plurality of LDs is disposed at a first distance from a surface of the object or an apparatus that is farther than a second distance at which one of the plurality of LEDs is disposed from the surface.

16. An apparatus configured to detect bio-information, the apparatus comprising:
a light-emitting diode (LED) and a laser diode (LD) configured to emit lights having different divergent angles on an object;
a plurality of light-receivers disposed to surround the LED and the LD, the plurality of light-receivers being configured to detect signals that are reflected by the object; and
a processor configured to process the signals to detect the bio-information of the object,
wherein the LED and the LD are further configured to emit the lights with a delay time,
wherein the LD is disposed at a first distance from a surface of the object or the apparatus that is farther than a second distance at which the LED is disposed from the surface, and
wherein the signals comprise photoplethysmogram signals or pulse waves of a surface of skin of the object.

* * * * *